US 6,415,784 B1

(12) United States Patent
Christrup et al.

(10) Patent No.: US 6,415,784 B1
(45) Date of Patent: Jul. 9, 2002

(54) INHALER

(75) Inventors: Søren Christrup, Struer; Anders Geert-Jensen, Højbjerg; Mikael Jørgensen, Århus C; Jørgen Rasmussen, Struer; Hugo Dines Schmidt, Århus C, all of (DK)

(73) Assignee: AstraZeneca AB, Sodertalje (SE)

( * ) Notice: Subject to any disclaimer, the term of this patent is extended or adjusted under 35 U.S.C. 154(b) by 0 days.

(21) Appl. No.: 09/424,335

(22) PCT Filed: Sep. 24, 1999

(86) PCT No.: PCT/SE99/01686

§ 371 (c)(1),
(2), (4) Date: Nov. 22, 1999

(87) PCT Pub. No.: WO00/16838

PCT Pub. Date: Mar. 30, 2000

(30) Foreign Application Priority Data

Sep. 24, 1998 (DK) ........................ 1998 01207

(51) Int. Cl.[7] ............................................. A61M 11/00
(52) U.S. Cl. ........................... 128/200.23; 128/200.12; 128/200.14; 128/203.12; 128/203.15
(58) Field of Search ........................ 128/200.12, 200.14, 128/200.23, 203.12, 203.15, 203.23

(56) References Cited

U.S. PATENT DOCUMENTS

| 3,456,644 A | * | 7/1969 | Thiel ................. | 128/200.23 |
| 3,598,294 A | * | 8/1971 | Hedrick et al. ........ | 222/402.2 |
| 3,814,297 A | * | 6/1974 | Warren ............... | 128/200.23 |
| 5,027,808 A | * | 7/1991 | Rich et al. ........... | 128/200.23 |
| 5,060,643 A | * | 10/1991 | Rich et al. ........... | 128/200.23 |
| 5,217,004 A | * | 6/1993 | Blasnik et al. ........ | 128/200.23 |
| 5,347,998 A | * | 9/1994 | Hodson et al. ........ | 128/200.23 |

FOREIGN PATENT DOCUMENTS

| GB | 12689811 A | * | 4/1972 |
| GB | 2263873 | * | 11/1993 |
| WO | WO-8201133 A1 | * | 4/1982 |

* cited by examiner

Primary Examiner—John G. Weiss
Assistant Examiner—Darwin P. Erezo
(74) Attorney, Agent, or Firm—Nixon & Vanderhye

(57) ABSTRACT

The actuation mechanism of a breath-actuated inhaler for delivery of a medicament by inhalation. The actuation mechanism includes a pre-loading mechanism is arranged to load the resilient loading element by manual depression of two contact members movable relative to the housing and disposed opposite one another on either side of the axis of a canister held in the housing. The actuation mechanism also includes a pivotably mounted trigger vane arranged to be moved by inhalation at the mouthpiece to cause operation of the actuation mechanism, wherein the trigger vane is mounted to pivot about an axis passing through the center of mass of the trigger. The triggering mechanism comprises a knee joint having a locked position where the knee joint holds the resilient loading element against compression of the canister and a trigger responsive to the inhalation at the mouthpiece to break the knee joint into a broken position where the knee joint releases the resilient loading element to allow compression of the canister. Furthermore the trigger comprises a second knee joint connected to the first-mentioned knee joint and having a locked position where the second knee joint holds the first knee joint in its locked position and movable in response to inhalation at the mouthpiece to a broken position to break the first knee joint.

10 Claims, 7 Drawing Sheets

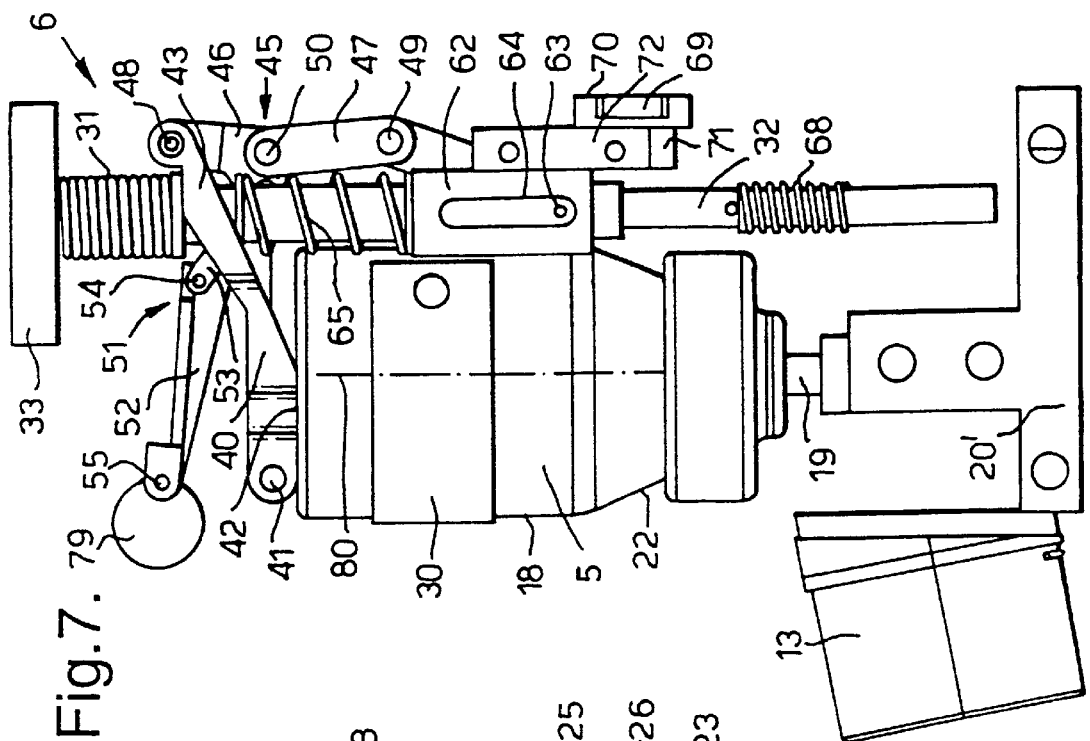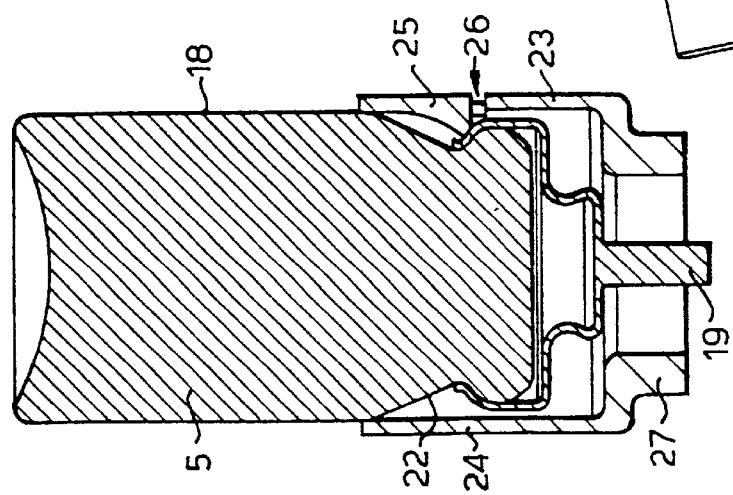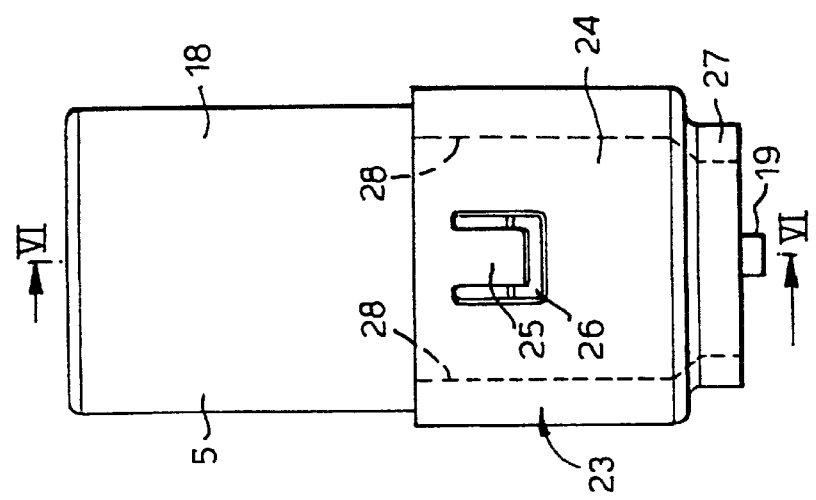

INHALER

The present invention relates to an inhaler for delivery of a medicament by inhalation and in particular to the actuation mechanism used in the inhaler used to actuate the canister to deliver a dose of medicament.

Known inhalers hold a canister of medicament which is actuatable by compression to deliver a dose of medicament Many known inhalers have been designed with an actuation mechanism to automatically actuate the canister. The present invention is concerned with optimising such an actuation mechanism.

Some known actuation mechanisms are breath-actuated, so that they operate in response to inhalation by a user. Typically, a breath-actuated inhaler includes a pre-loading mechanism for loading a resilient loading element with an actuation force which is used to bias compression of the canister, in combination with a triggering mechanism arranged to hold the resilient loading element against compression of the canister and thereby store the actuation force. When delivery of a dose is required, the triggering mechanism releases to allow compression of the canister in response to inhalation by the user.

A problem often encountered, especially by elderly, young or infirm users, is that it is difficult to generate enough force to load the actuation mechanism, for example the resilient loading element if a pre-loading mechanism is provided. Clearly the energy provided must be at least that needed to actuate the canister and in fact the provision of an actuation mechanism means that additional energy must be applied as there will inevitably be energy wastage in any mechanism. The first aspect of the present invention is intended to assist in loading of the pre-loading mechanism.

One solution to this problem would be to provide a dispenser where the force required to actuate the canister is generated by an electric motor, but that suffers from the serious disadvantage that the inhaler ceases to operate when the motor power supply runs out. This is highly undesirable in the dispensing of medicaments.

According to the present invention, there is provided an inhaler for delivery of a medicament by inhalation, comprising:

a housing for holding a canister of medicament having a generally cylindrical body and a valve stem with the cylindrical axis of the body in a predetermined direction, the body and valve stem being compressed together to actuate the canister to deliver a dose of medicament from the valve stem;

an actuation mechanism arranged to receive energy for compressing the canister by manual depression of two contact members movable relative to the housing and disposed opposite one another on either side of the axis of a canister held in the housing.

By providing the contact members opposite one another on either side of the axis of the canister, the inhaler becomes far easier to load. The inhaler may be held in the palm of one hand and the two contact members depressed by a finger and thumb which allows the force to be easily applied. The inhaler may even be laid on a surface such as a table with one contact member touching the surface and the opposite contact member raised upwardly to allow the user to apply force by leaning on the inhaler and/or using both hands.

Preferably, the distance between the extremities of the contact members before depression is less than the maximum length of the inhaler in a direction parallel to the axis of canister held in the housing or is less than the overall length of the canister including the body and the valve stem.

Many known inhalers are arranged to load the resilient loading element by application of force along the axis of the canister, in which case there is a long distance between the parts which must be relatively moved, typically the length of the inhaler in a direction parallel to the axis of the canister and is longer than the overall length of the canister. This hinders the application of force because it is difficult to grip both contact surfaces especially for a person having relatively small hands. In contrast the present invention allows the movable parts to be closer together and hence more easily manipulated. The distance between the extremities of the buttons may be less than 95%, 90%, 85%, 80% or preferably 75% of the overall length of the canister. valve stem of the canister are relatively compressed to actuate the canister. By providing such gearing within the actuation mechanism, the size of the force which must be applied to the contact members may be reduced as compared to a system applying force over the distance by which the canister is compressed, because the energy required to be stored is the same in both cases. Desirably, the total distance over which the two contact members move is 2 times, 3 times, 5 times or preferably 8 or 10 times the canister compression distance A breath-actuated inhaler is typically stored in a loaded state in which the resilient loading element stores the actuation force. It is therefore the intention of the second aspect of the invention to provide a triggering mechanism which resist accidental operation.

According to a second aspect of the present invention, there is provided a breath-actuated inhaler for delivery of a medicament by inhalation, comprising:

a housing defining a mouthpiece and arranged to hold a canister of medicament actuatable to deliver a dose of medicament;

an actuation mechanism arranged to be operated to actuate the canister and including a pivotably mounted trigger vane arranged to be moved by inhalation at the mouthpiece to cause operation of the actuation mechanism, wherein the trigger vane is mounted to pivot about an axis passing through the center of mass of the trigger.

Such an arrangement of the triggering mechanism reduces the chance of accidental triggering due to a shock, for example if the inhaler is dropped. Any forces applied to the inhaler act on the trigger vane through the pivot, but in the present invention this does not create any torque tending to pivot the trigger vane because the pivot is also the center of mass.

A convenient structure for the trigger vane is to constitute it by a vane portion extending outwardly from the axis of the trigger vane to be moved by an air flow created by inhalation at the mouthpiece and a counterweight portion disposed on the opposite side of the axis of the trigger vane from the vane portion.

Whilst accidental triggering is undesirable, it is critical that a breath-actuated inhaler never fails when the user inhales. This is particularly important in an emergency where delivery of the medicament could be critical to the health or even the life of the user. The force provided by inhalation is relatively small compared to the force required to actuate the canister, so it is a difficult technical problem to devise a structure for the triggering mechanism which safely holds the stored actuation force without tending to trigger accidentally, whilst ensuring that triggering does occur when inhalation actually occurs. The third aspect of the present invention is intended to meet this design requirement. It would also be desirable to provide a triggering mechanism which achieves this balance with a large tolerance window for manufacturing the components of the triggering mechanism.

According to a third aspect of the present invention there is provided a breath-actuated inhaler for delivery of a medicament by inhalation, comprising a housing having a mouthpiece and arranged to hold a canister of medicament actuatable to deliver a dose of medicament from the mouthpiece by compression of the canister, and an actuation mechanism for actuating the canister, comprising:

a pre-loading mechanism for loading a resilient loading element with an actuation force, the resilient loading being element being arranged when loaded to bias compression of the canister, a triggering mechanism comprising a knee joint having a locked position where the knee joint holds the resilient loading element against compression of the canister and a trigger responsive to the inhalation at the mouthpiece to break the knee joint into a broken position where the knee joint releases the resilient loading element to allow compression of the canister, wherein the trigger comprises a second knee joint connected to the first mentioned knee joint and having a locked position where the second knee joint holds the first knee joint in its locked position and movable in response to inhalation at the mouthpiece to a broken position to break the first knee joint.

Such use of two knee joints connected together in such a ganged relationship has been found to meet the design requirement discussed above of ensuring triggering upon inhalation whilst limiting the chances of accidental triggering. In particular, the first knee joint is safely held against accidental triggering by the second knee joint in the locked state but the pair of knee joint respond positively to inhalation by the user to release the triggering mechanism and actuate the cannister. This effect may be achieved within comparatively relaxed tolerances for the parts of the mechanism. This ensures that the inhaler delivers a dose or inhalation, even if the parts form over time.

Preferably the second knee joint has a plurality of jointed links, at least one of which is a trigger vane movable by inhalation at the mouthpiece. This allows the triggering mechanism to respond actively to inhalation.

Desirably the pre-loading mechanism further comprises a pivotable lever biased by the resilient loading element to compress the cylinder through a portion coupled to the canister, the first knee joint being connected to the lever A for holding the resilient biasing element. Use of a lever to compress the cannister allows leverage to be obtained between the compressional force on the cannister, the resilient biasing element and the locking mechanism. This assists in allowing the forces within the pre-loading mechanism to be controlled by the triggering mechanism, thereby enhancing the effect of triggering mechanism.

Advantageously, the first knee joint is connected to the lever at a position further away from the pivot of the lever than the portion through which the lever is coupled the canister.

Advantageously, the resilient loading element biases the lever at a position further away from the pivot than the portion through which the lever is coupled to the canister.

To allow a better understanding, an inhaler which embodies the present invention will now be described by way of non-limitative example with reference to the accompanying drawings, in which:

FIG. 5 is a side view of an alternative form of collar for connecting the closure element to the canister;

FIG. 6 is a cross-sectional view taken along line VI—VI in FIG. 5;

FIG. 7 is a side view of the canister mounting arrangement and actuation mechanism;

Figure 1:
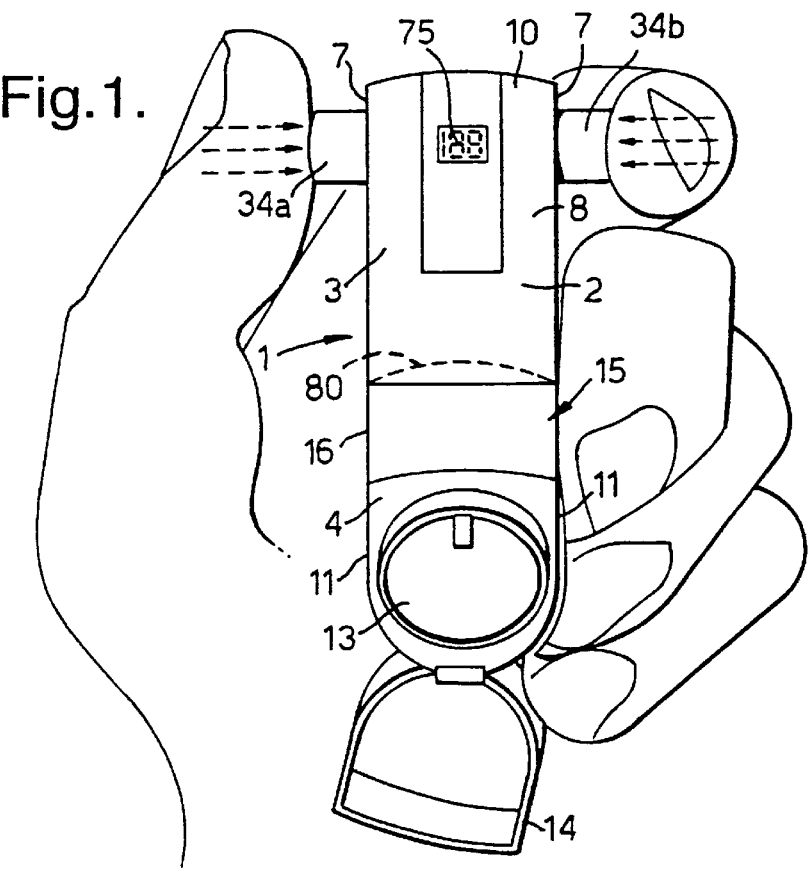
FIG. 1 is a front view of the inhaler held in a hand.
Figure 2:
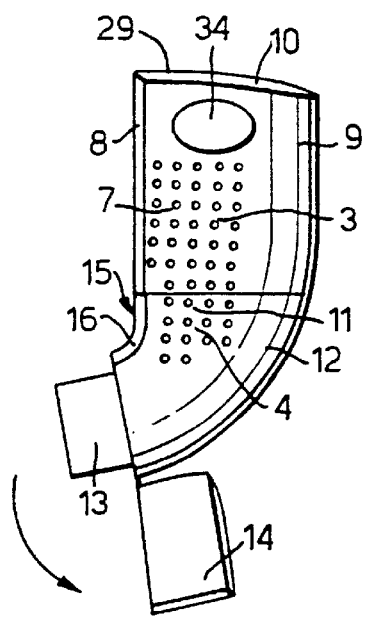
FIG. 2 is a side view of the inhaler.

An inhaler 1 which embodies the present invention is illustrated in FIGS. 1 and 2, respectively showing the front view of the inhaler 1 held in a user's hand and a side view of the inhaler.

The inhaler has a housing 2 comprising an upper housing portion 3 and a lower housing portion 4 which are coupled together. The upper and lower housing portions 3 and 4 have outer walls which are hollow to defame a space accommodating a canister 5 of medicament and an actuation mechanism 6 operatable to actuate the canister 5 to deliver a dose of medicament.

The upper housing portion 3 has opposed side walls 7 joined by a flat front wall 8, a curved rear wall 9 and a top wall 10. The lower housing portion 3 has opposed side walls 11 fitting flush with the side walls 7 of the upper housing portion 3 and a curved rear wall 12 fitting flush with the rear wall 9 of the upper housing portion 3. The rear walls 12 and 9 together form a curved surface comfortably received in the palm of the user's hand as illustrated in FIG. 1. A mouthpiece 13 protrudes from the lower housing portion 4 and may be protected by a cap 14 hinged to the lower housing member 4 to be openable as illustrated in FIG. 2.

The front of the lower housing member 4 between the side walls 11 is open to define a vent in the outer surface of the housing 2 adjacent the mouthpiece 13 between the upper and lower housing portions 3 and 4. The vent 15 is closed by a closure element 16 fitting flush with the front wall 8 of the upper housing portion 3 to form part of the outer wall of the housing 2.

Figure 3:
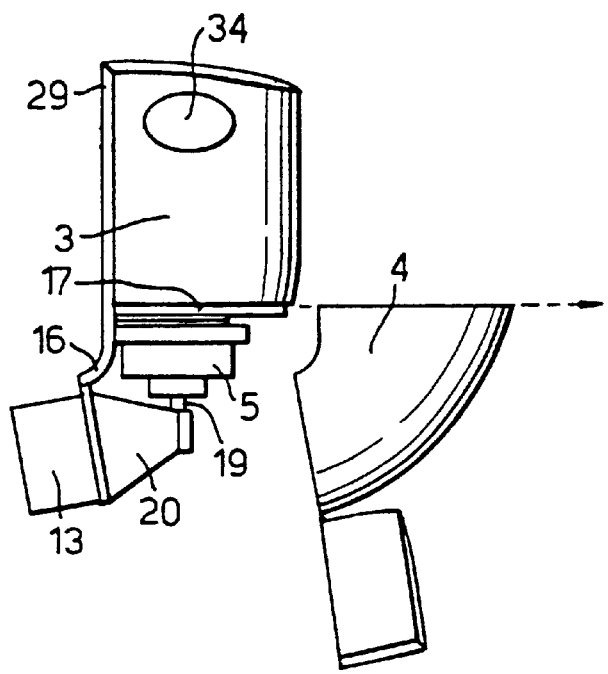
FIG. 3 is a side view of the inhaler with a lower housing portion being removed.

The upper and lower housing members are coupled by a coupling 17 allowing the lower housing member 4 to be slid off as illustrated in FIG. 3.

Figure 4:
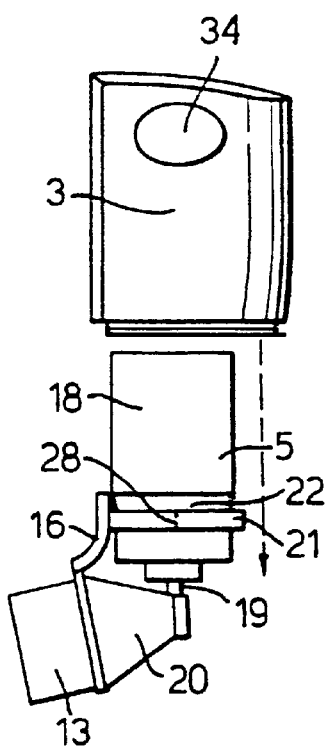
FIG. 4 is a side view of an upper housing portion of the inhaler with a canister being removed.

The canister 5 fits in the upper housing portion 3 and may be slidably removed for replacement as illustrated in FIG. 4.

The canister 5 comprises a generally cylindrical body 18 and a valve stem 19 which are compressible together to deliver a dose of medicament from the valve stem 19. The canister is of a known type including a metering chamber which captures a defined volume of medicament from the body 18 of the canister 5, which volume of medicament is delivered as a metered dose from the valve stem 19 on compression of the valve stem 19 relative to the body 18. The valve stem 19 is weakly biassed outwardly to reset the canister 5 after compression for refilling the metering chamber. The valve stem 19 is received in a nozzle block 20 which is arranged to direct a dose of medicament delivered from the valve stem 19 out of the inhaler 1 through the mouthpiece 13.

The closure element 16 is connected to the canister 5 by a collar 21 fitted around a necked portion 22 of the canister body 18. The collar 21 is permanently fixed to the closure element 16 and may be integral therewith. The collar 21 is restrained by the necked portion 22 of the canister 5 such that the closure element 16 is removed and replaced together with the canister 5 as illustrated in FIG. 4. The canister 5 and collar 21 have a small degree of relative movement along the axis of the canister 5. This allows actuation of the canister by compression of the canister body 18 towards the valve stem 19 when the stem 19 is fixed relative to the inhaler 1 in the nozzle block 20 and the collar 21 is also fixed by the closure element 16 fitting as part of the housing 2 of the inhaler 1.

FIGS. 5 and 6 respectively illustrate a side view and cross-sectional view and alternative collar 23 for connecting the closure element 16 to the canister 5. The collar 23 includes a cylindrical portion 24 held on the necked portion 22 of the canister body 18 by a protrusion 25 formed in the cylindrical portion 24 by a U-shaped cut-out 26. The cylindrical portion 24 has an extension 27 extending beyond the end of the canister body 18 to protect the valve stem 19. The extension 27 is of reduced diameter relative to the remainder of the cylindrical portion 24 of the collar 23.

The collars 21 and 23 are both formed with a weak portion constituted by two rupture lines 28 disposed on opposite sides of the collar 21 or 23 and arranged to be broken preferentially to the remainder of the collar 21 or 23 on application of a force to separate the closure element 16 from the canister 5. After the rupture lines 28 have been broken or at least deformed to enable removal of the canister 5, it is impossible to connect the collar 21 or 23 to a different canister.

The outer surface of the closure element 16 carries an indication of the type of medicament in the canister 5 to which the closure element 16 is connected. The indication may be printed information, an embossed or indented pattern or the colour of the closure element 16.

An inlet opening 29 is formed in the upper housing portion 3, in particular in its top wall 10 and front wall 8. The outer walls of the housing defamed by the upper and lower portions 3 and 4 and the closure element 16 seal together to define a closed space which constitutes an air flow path extending from the mouthpiece 13 through the housing 2 to the inlet opening 29. Inhalation at the mouthpiece 13 draws air in through the inlet opening 29 through that air flow path around the canister 5 and actuation mechanism 6 encased in the housing 2. The actuation mechanism 6 (described in detail below) has a trigger disposed in the upper housing portion 4 which, in response to a flow through the air flow path, triggers the actuation mechanism 6 to actuate the canister 5.

Figure 2A:
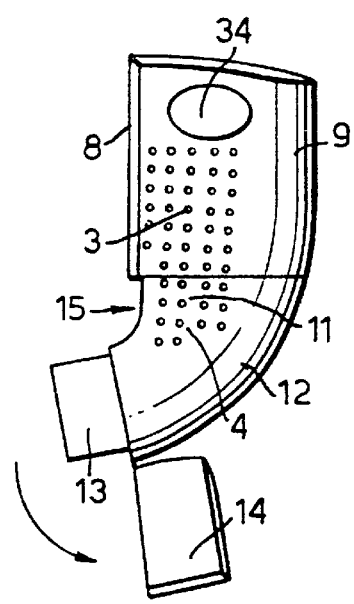
FIG. 2A is a side view of the inhaler without a closure element fitted.

If a canister without a closure element connected thereto is inserted into the housing 2, then the vent 15 will remain open as illustrated in FIG. 2A. Consequently, when a user inhales at the mouthpiece 13, the flow resistance through the vent 15 will be much lower than the flow resistance through the remainder of the air flow path above the vent 15 from the inlet opening 29. Accordingly, the vent 15 will vent most of the flow through the mouthpiece, thereby reducing the flow in the remainder of the air flow path in the upper housing portion through. The positioning of the vent 15 in the air flow path inside the housing 2 between the mouthpiece 13 and the trigger reduces the air flow across the trigger. The vent 15 is positioned and dimensioned such that the flow at the trigger is reduced below the threshold needed to operate the trigger and therefore prevents operation of the actuation mechanism 6. To assist in assuring that the vent 15 sufficiently vents the flow, the vent 15 is provided with a larger opening area and hence a lower flow resistance than the inlet opening 29. The vent 15 is dimensioned so that the actuation mechanism is not operated on a flow through the mouthpiece 13 at a level above the maximum expected inhalation, for example at an inhalation of at least eight times a standard inhalation flow rate. The triggering mechanism for the actuation mechanism 6 is designed taking into account the flow generated by a standard inhalation selected by the designer.

Figure 8:
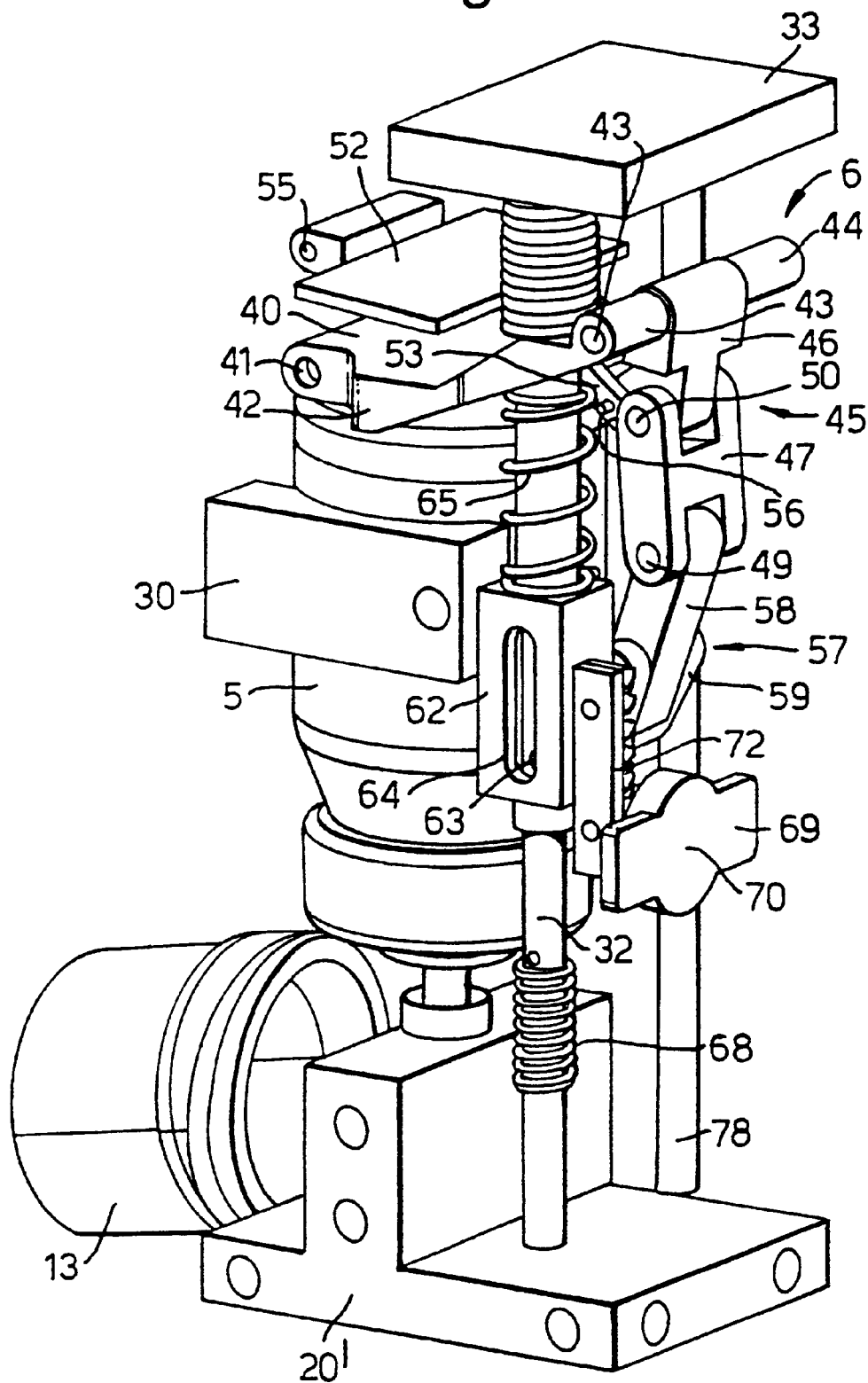
FIG. 8 is a view from the rear and side of the actuation mechanism.
Figure 9:
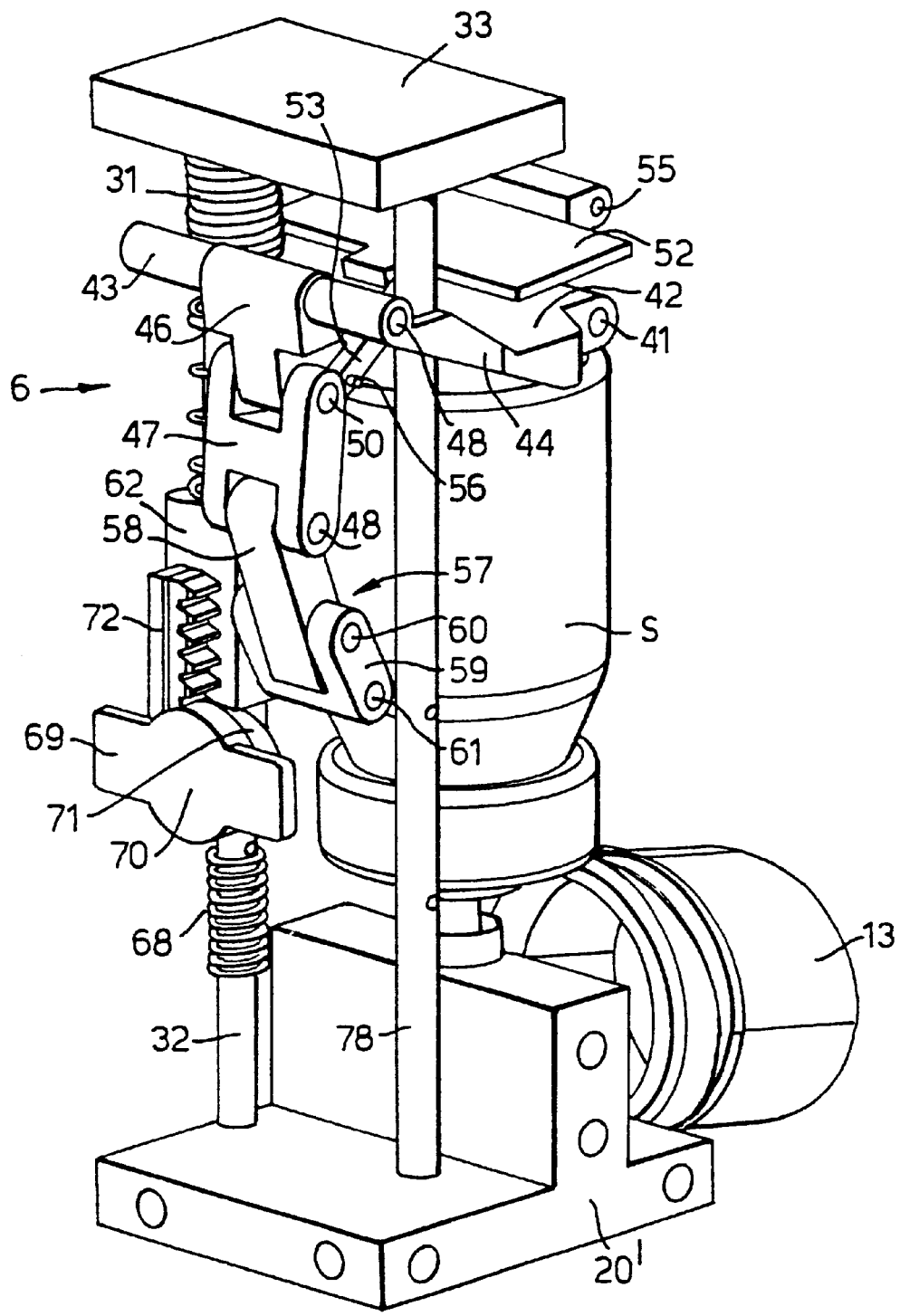
FIG. 9 is a view from the rear and the opposite side from FIG. 8 of the actuation mechanism.

The actuation mechanism 6 for actuating the canister 5 to deliver a dose of medicament is illustrated in FIGS. 7 to 9. The elements illustrated in FIGS. 7 to 9 are accommodated in the housing 2 but are illustrated separately for clarity. The canister 5 is held with its valve stem 19 in a nozzle block 20' connected to the mouthpiece 13, both fixed relative to the lower housing portion 4. A nozzle block 20' has a slightly different structural form from the nozzle block 20 illustrated in FIGS. 3 and 4 but performs the same function. The body 18 of the canister 5 is supported by a guide block 30 fixed to the upper housing portion 3 and having a curved inner surface engaging the cylindrical surface of the canister body 18 to allow axial movement of the canister body 18 within the housing 2. The actuation mechanism 6 operates to compress the canister body 18 relative to the valve stem 19 held in the nozzle block 20 to deliver a dose of medicament.

The structure of the actuation mechanism 6 is as follows.

The actuation mechanism 6 includes a pre-loading mechanism for loading a resilient loading element in the form of a coiled loading spring 31. The pre-loading mechanism includes the loading member constituted by a shaft 32 encircled by the coils of the loading spring 31. The shaft extends and is movable in a direction parallel to the cylindrical axis 80 of the canister body 18. The loading member shaft 32 has an enlarged head 33.

As illustrated in FIG. 1, two buttons 34a and 34b, constituting contact members to be manually depressed, are mounted opposite one another in the side walls 7 of the upper housing portion 3 on either side of the axis 80 of the canister 5 held in the housing 2. The buttons 34 are manually depressible in a direction substantially perpendicular to the axis 80 of the cannister 5 which makes them easy to grip and move by a finger and thumb, as can be seen in FIG. 1. The distance between the extremities of the buttons 34 before depression as illustrated in FIG. 1 is less than the length of the inhaler along the axis of the container (vertical in FIG. 1) and is less than the overall length of the canister 5 including the body 18 and the stem 19. This improves the ergonomics and makes the inhaler easier to load as compared to an inhaler loaded by application of force along the length of the cannister.

The buttons 34 are depressible to be flush with the housing 2. As a result of the gearing inherent in the actuation mechanism, the total distance of movement of both buttons is greater than the distance which the body 18 and the valve stem 19 of the canister 5 are relatively compressed.

Figure 10:
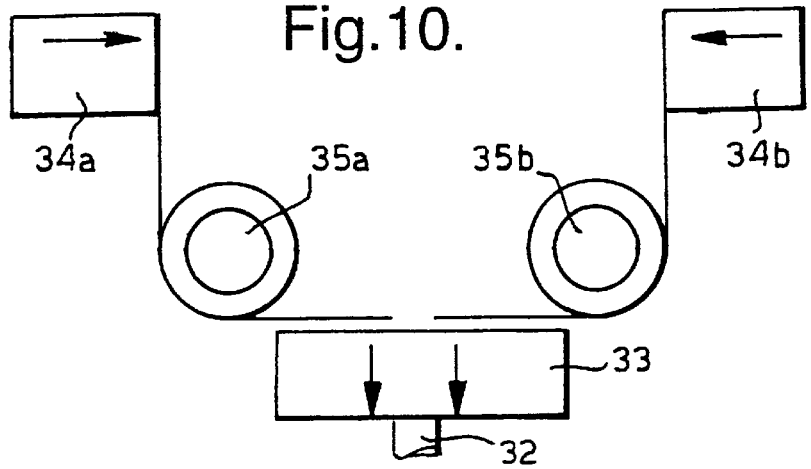
FIG. 10 is a front view of the arrangement for loading the actuation mechanism.

The buttons 34 load the loading member 32 and loading spring 31 through the arrangement illustrated in FIG. 10 comprising two torsion springs 35a and 35b fixed inside the upper housing portion. The torsion springs 35a and 35b engage the enlarged head 33 of the loading member 32 and respective ones of the buttons 34 to convert sideways force applied to the buttons 34 to a downwards force along the axis of the loading member shaft 32.

Figure 11:
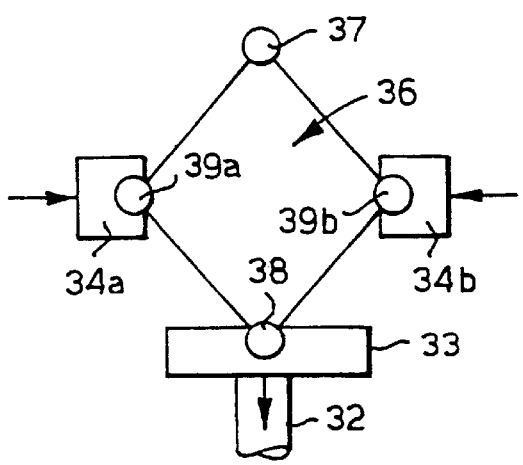
FIG. 11 is a side view of an alternative form of button arrangement for loading the actuation mechanism.

An alternative means for converting the sideways force applied to the buttons 34 is illustrated in FIG. 11. This consists of a double knee joint 36 fixed at its upper end 37 to the upper housing portion 3, fixed at its lower end 38 to the enlarged head 33 of the loading member 32 and fixed at its intermediate joints 39a and 39b to the respective buttons 34a and 34b.

The pre-loading mechanism further includes a lever 40 pivoted relative to the housing about a pivot 41. The lever 40 has a planar canister engagement portion 42 contacting the canister body 18 adjacent the pivot 41 with a pair of arms 43 and 44 extending therefrom. One arm 43 is engaged by the loading spring 31 so that the loading spring 31, when loaded, biases compression of the canister through the lever 40 coupled to the canister 5 by the canister engagement portion 42. As the loading spring 31 is further away from the pivot 41 than the cannister engagement portion 42, this provides leverage between the loaded actuation force and the force applied to the cannister 5. The arm 43 has a hole through which the loading member shaft 32 extends. The other arm 44 of the lever 43 has a similar hole through which extends a further shaft 78 for preventing lateral displacement of the lever 40.

The actuation mechanism further includes a triggering mechanism for holding the lever 40 against compression of the canister under the biasing of the spring 31 and to release the lever 40 in response to inhalation at the mouthpiece. The triggering mechanism is constructed as follows.

The triggering mechanism comprises a first knee joint 45 having two links 46 and 47 connected pivotally to one another by a central pivot 50. The upper link 46 is pivotally connected both arms 43 and 44 of the lever 40 by a pivot 48. The lower link 47 is pivotally connected to the upper housing portion 3 by a pivot 49.

Accordingly, the first knee joint 45 has a locked position illustrated in FIGS. 7 to 9 in which it holds the lever 40 against compression of the canister 5. In the locked position of the first knee joint 45, the central pivot 50 is substantially aligned with the pivots 48 and 49 at the ends of the links 46 and 47. As the first knee joint 45 is connected to the lever at a position further away from the pivot 41 then the cannister engagement portion 42, this provides leverage between the locking force provided by the first knee joint and the force applied to the cannister 5. This leverage enhances the locking and triggering action of the triggering mechanism.

The triggering mechanism further includes a second knee joint 51 comprising two links 52 and 53 connected by a central pivot 54. One link 57 of the second knee joint 51 is pivotally connected to the upper housing portion 3 by a pivot 55 and extends laterally so that it constitutes a trigger vane which is moved by a flow of air thereover. The trigger vane 52 has a counterweight portion 79 (illustrated only in FIG. 7) fixed to the opposite side of pivot 55 from the laterally extending surface. The counterweight balances the trigger vane so that its center of mass is positioned on the axis of the pivot 55.

The other link 53 of the second knee joint 51 extends from the trigger vane 52 between the arms 43, 44 of the lever 40 to the upper link 46 of the first knee joint 45 where it is pivotally connected by a pivot 56.

Accordingly, the second knee joint 51 has a locked position illustrated in FIGS. 7 to 9. In the locked position of the second knee joint, the central pivot 54 is substantially aligned with the pivots 55 and 56 and the ends of the links 52 and 53.

The actuation mechanism 6 further includes a reset mechanism which is constructed as follows.

The reset mechanism employs a locking element constituted by a third knee joint 57 comprising an upper link 58 and a lower link 59 pivotally connected together by a central pivot 60. The upper link 58 is pivotally connected to the upper housing portion 3 by the pivot 49 in common with the first knee joint 45. The lower link 59 is pivotally connected to the loading member shaft 32 by a pivot 61. The third knee joint 57 has a locked position illustrated in FIGS. 7 to 9 in which it holds the loading member shaft 32 in its loaded position as illustrated in FIG. 7. In the locked position of the third knee joint 57, the central pivot 60 is aligned with the pivots 48 and 61 at the end of the links 58 and 59. The third knee joint 57 is also biased into its locked position by a biasing spring 67 connected to the upper housing portion 3. Hence the third knee joint constitutes a locking element which holds the canister in a compressed state through spring 31 and lever 40 after the full movement of the lever 40 to compress the canister 5.

The reset mechanism further includes a release member 62 mounted on the loading member shaft 32 by having an aperture through which the shaft 32 extends. The release member 62 is movable relative to the shaft 32 between limits defined by a pin 63 protruding from the shaft 32 engaging in a track 64 formed in the release member 62. A timer spring 65, the coils of which encircle the shaft 32, is connected between the arm 43 of the lever 40 and the release member 62. The timer spring 65 is in a relaxed state in FIG. 7 and is provided for biasing the release member 62 when loaded by movement of the lever 40 to compress the canister 5.

Figure 12:
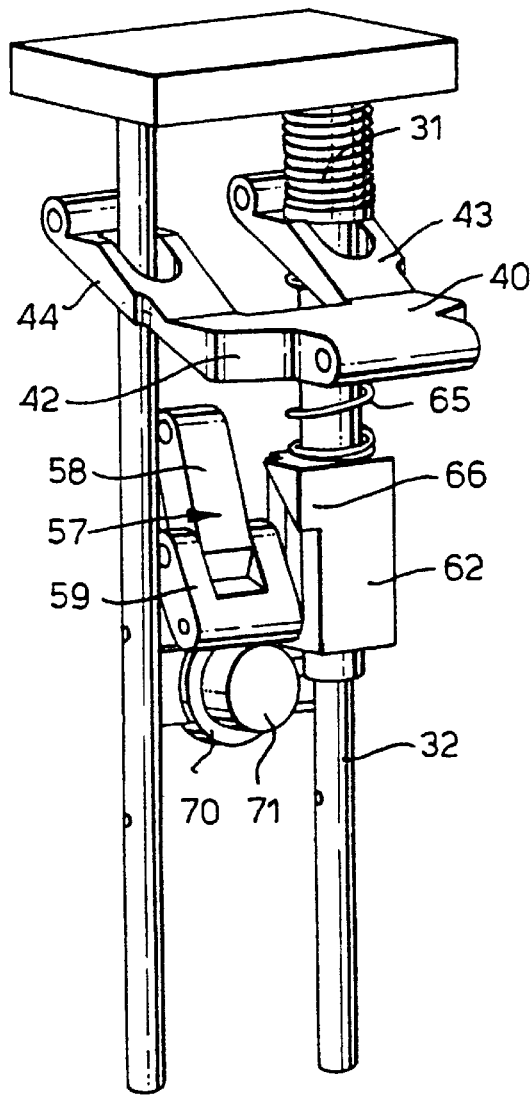
FIG. 12 is a view of certain parts of the actuation mechanism from the front and side.

A protrusion 66 extends from the release member 62 (as best seen in the partial view of FIG. 12) to engage with the lower link 59 of the third knee joint 57 when the release member 62 is moved down the shaft 32. Such engagement of the protrusion 56 with the third knee joint 57 moves the knee joint 57 against the biasing spring 67 to break the third knee joint 57 thereby releasing locking effect of the third knee joint 57.

The shaft 32 is biased upwardly by a reset spring 68 acting between the shaft 32 and upper housing portion 3 to move the shaft 32 upwardly upon H breaking of the third knee joint 57.

The downwards movement of the release member 62 is damped by a damping element 69 consisting of a stator 70 fixed to the upper housing portion 3 and a rotor 71 rotatable through viscous fluid provided between the rotor 71 and stator 70. The rotor 71 is driven by a toothed rack 72 connected to the release member 62.

Operation of the actuation mechanism 6 will now be described with reference to FIGS. 13 to 16 which illustrate the various parts of the actuation mechanism 6 in schematic form for ease of understanding.

Figure 13:
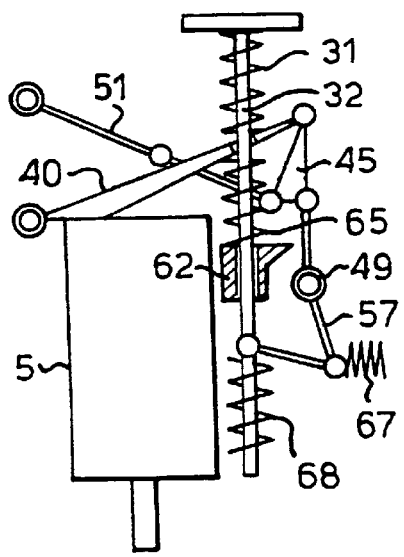
FIGS. 13 to 16 are schematic views of the actuation mechanism illustrating respective states over a complete cycle of operation.

FIG. 13 illustrates the neutral state in which the loading member shaft 32 is in its uppermost position, so that the loading spring 31 is relaxed. In this state, the first and second knee joints 45 and 51 are both in their locked positions. The timer spring 65 and the reset spring 68 are relaxed.

Figure 14:
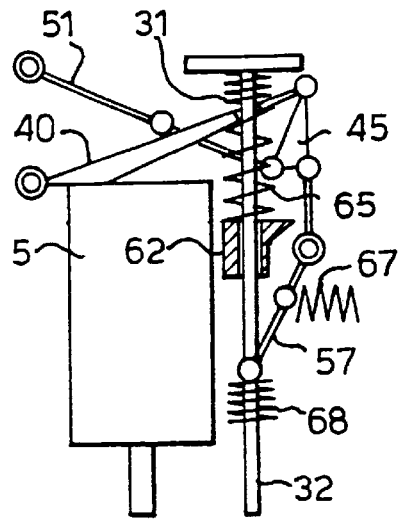
Figure 15:
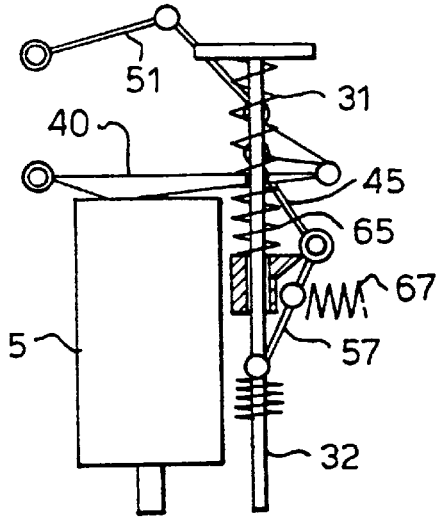

Upon depression of the buttons 34, the loading member shaft 32 is moved downwardly to a second position illustrated in FIG. 14 loading the loading spring 31 which therefore biases the lever 40 towards compression of the canister 5. However, the first knee joint 45 is its locked position where it holds the lever 40 against compression of the canister 5. The first knee joint 45 is held in its own locked position by the second knee joint 51 being in its locked position.

Movement of the loading member shaft 32 downwards also loads the reset spring 68 and brings the third knee joint 57 into its locked position where it is held by the spring 67. In this loaded state illustrated in FIG. 14, the inhaler 1 is loaded ready for delivery of a dose of medicament.

Inhalation by the user at the mouthpiece 13 generates an air flow through the air flow path defined inside the housing 2 from the inward opening 29 to the mouthpiece 13. This air flow acts on the trigger vane 55 of the second knee joint 51 causing it to move upwardly due to pressure drop created by the flow inside the housing 2 to the position illustrated in FIG. 15 where the second knee joint is broken. This breaks the first knee joint 45 into its broken position illustrated in FIG. 15 which releases the lever 40 and allows it to compress the canister 5 under the biasing of the loading spring 31.

During compression of the canisters, the shaft 32 remains locked in position by the third knee joint 57. This causes the canister to be held in its compressed state by the shaft 32 acting through the spring 31 and lever 40, the spring force of the spring 31 far exceeding the internal reset biasing of the canister 5.

Figure 16:
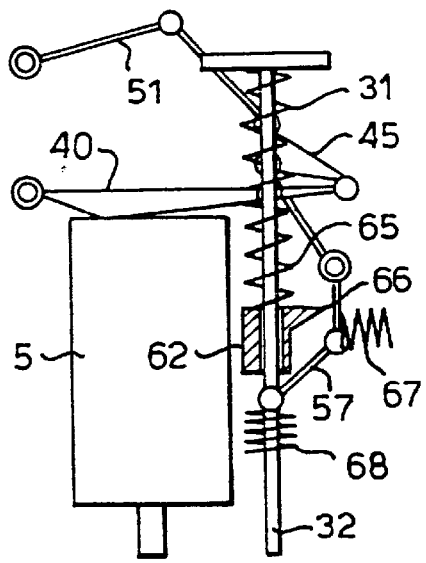
Figure 17:
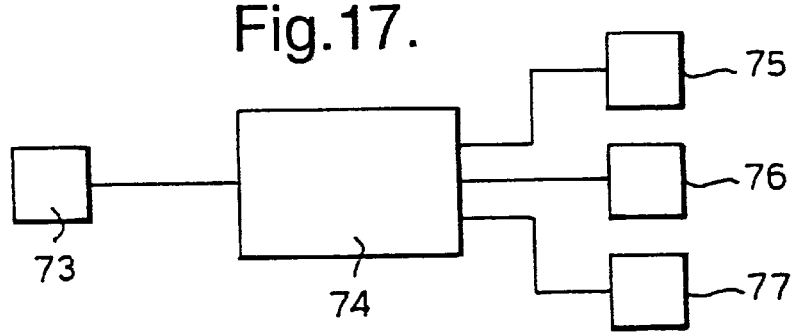
FIG. 17 is a view of the electronic timer circuit.

However, movement of the lever 40 loads the timer spring 65 which accordingly biasses the release member 62 downwards. Movement of the release member 62 is delayed by the damping action of the damping element 69. The protrusion 66 of the release element 62 engages the third knee joint 57 after a predetermined period of time after actuation of the canister 5. This time is determined by the strength of the timer spring 65 and the damping properties of the damping element 69 and is at least 100 ms or 200 ms and up to 1000 ms or 5000 ms to allow the full dose of medicament to be delivered from the cannister 5. Such engagement breaks the third knee joint 57 into its broken position as illustrated in FIG. 16. Subsequently the reset spring 68 moves the loading member shaft 32 upwardly to the neutral position illustrated in FIG. 13. At the same time the shaft 32 lifts the release member 62, itself still damped by the damping element 69 so that the reset movement is damped.

Release of the shaft 32 causes the spring 31 to raise the lever 40 which has two effects. Firstly it allows the canister to reset itself. Secondly, it causes the first and second knee joints 45 and 51 to straighten, returning them to their locked position in the neutral position of the actuator mechanism illustrated in FIG. 13. The loading spring 31 and the timer spring 65 are pre-loaded and do not work against the reset movement, so that the reset spring 68 has only to overcome friction and the weight of the component.

The buttons 34a and 34b protrude from the inhaler when the actuation is in its relaxed state as shown in FIG. 1 and are depressed to a position flush with the side walls 8 of the upper housing portion 3. Accordingly, the distance between the extremities of the buttons before depression is less than the maximum length of the inhaler 1 in the direction parallel to the axis 80 of the canister 5 and less than the overall length of the canister 5 including the body 18 and the valve stem 19. Also, the total distance over which the two buttons 34 are moved relative to one another is greater than the distance by which the body 18 and the valve stem 19 of the canister 5 are relatively compressed. This is achieved by the leverage obtained by the loading spring 31 engaging lever 40 at a point further away from the pivot 41 than the canister engagement portion 42.

The actual flow recommended in order to correctly deliver a drug will depend on the manner operation of the drug, the position where it should be deposited in the mouth, lungs of the user and the manner of dispensing the drug. Some drugs are inhaled as a fine mist and transported all the way to the lungs whereas others are inhaled like a jet of liquid deposited in the mouth of the person. These different types of drugs require different types of inhalation and therefore different inhalation flows and different actions by the user.

It is possible to adapt each of a number of different inhalers for use with a number of different types of drug by giving each inhaler a vent with a different shape and giving different closure elements shapes which conform with a single type of inhaler. For example, a possible different shape is illustrated by the dotted line in FIG. 1. Thus canister with differently shaped closure elements are for use exclusively with the inhaler having a conforming vent. The different shapes may prevent a closure element from being fitted in an inhaler of the inhaler having a conforming vent. Alternatively, the closure element may fail to close the vent of an inhaler having a differently shaped vent such that the remaining opening vents the flow sufficiently to prevent operation of the triggering mechanism.

What is claimed is:

1. An inhaler for delivery of a medicament by inhalation, comprising:
   a housing for holding a canister of medicament, said canister when present having a generally cylindrical body with a cylindrical axis and a valve stem, said cylindrical axis of the body being in a predetermined direction, the body and valve stem being compressed together to actuate the canister to deliver a dose of medicament from the valve stem; and
   an actuation mechanism arranged to receive energy for compressing the canister by manual depression of two contact members movable relative to the housing and disposed opposite one another transversely on either side of a cylindrical axis of a canister held in the housing.

2. An inhaler according to claim 1, wherein the contact members have extremities separated by a distance which before depression is less than the maximum length of the inhaler in a direction parallel to the axis of canister held in the housing.

3. An inhaler according to claim 1, wherein the contact members have extremities separated by a distance which before depression is less than the overall length of the canister including the body and the valve stem.

4. An inhaler according to claim 1, wherein the two contact members are moved relative to one another by a total distance which is greater than the distance by which the body and the valve stem of the canister are relatively compressed to actuate the canister.

5. An inhaler according to claim 1, wherein the contact members are buttons protruding from the housing before depression.

6. An inhaler according to claim 1, wherein the actuation mechanism comprises a pre-loading mechanism arranged to load a resilient loading element with an actuation force by depression of said contact members, the resilient loading element, when loaded, being arranged to bias compression of the canister,
   a triggering mechanism arranged to hold the resilient loading element against compression of the canister and to release the triggering mechanism to allow compression of the canister.

7. A breath-actuated inhaler for delivery of a medicament by inhalation, comprising
   a housing having a mouthpiece and arranged to hold a canister of medicament actuatable to deliver a dose of medicament from the mouthpiece by compression of the canister, and an actuation mechanism for actuating the canister, comprising:
- a pre-loading mechanism for loading a resilient loading element with an actuation force, the resilient loading element being arranged when loaded to bias compression of the canister,
- a triggering mechanism comprising a first knee joint having a locked position where the knee joint holds the resilient loading element against compression of the canister and a trigger responsive to the inhalation at the mouthpiece to break the knee joint into a broken position where the knee joint releases the resilient loading element to allow compression of the canister,
- said trigger comprising a second knee joint connected to the first knee joint and having a locked position where the second knee joint holds the first knee joint in its locked position and movable in response to inhalation at the mouthpiece to a broken position to break the first knee joint,
- said pre-loading mechanism further comprising a pivotable lever biased by the resilient loading element to compress the canister through a portion coupled to the canister, the first knee joint being connected to a lever for holding the resilient loading element, said pivotable lever being coupled to the canister by a portion contacting the canister.

8. An inhaler according to claim 7, wherein the second knee joint has a plurality of jointed links, at least one of which is a trigger vane movable by inhalation at the mouthpiece.

9. An inhaler according to claim 7, wherein the first knee joint is connected to the lever at a position which is further from the pivot of the lever than the portion through which the lever is coupled to the canister.

10. An inhaler according to claim 7, wherein the resilient loading element biases the lever at a position which is further from the pivot than the portion through which the lever is coupled to the canister.

* * * * *